(12) United States Patent
Inokuchi et al.

(10) Patent No.: US 9,616,254 B2
(45) Date of Patent: Apr. 11, 2017

(54) AQUEOUS DISPERSION COMPRISING SILICONE ELASTOMER PARTICLES, A SILICONE ELASTOMER PARTICLE AND A COSMETIC

(71) Applicant: SHIN-ETSU CHEMICAL CO., LTD., Tokyo (JP)

(72) Inventors: Yoshinori Inokuchi, Annaka (JP); Ryuji Horiguchi, Annaka (JP); Chihiro Hayakawa, Tokyo (JP); Masayuki Konishi, Tokyo (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 28 days.

(21) Appl. No.: 14/526,028

(22) Filed: Oct. 28, 2014

(65) Prior Publication Data
US 2015/0118320 A1 Apr. 30, 2015

(30) Foreign Application Priority Data
Oct. 29, 2013 (JP) .................................. 2013-224417

(51) Int. Cl.
| | |
|---|---|
| *A61K 9/50* | (2006.01) |
| *A61Q 1/02* | (2006.01) |
| *A61K 8/86* | (2006.01) |
| *C08L 83/04* | (2006.01) |
| *C08L 83/14* | (2006.01) |
| *A61Q 19/00* | (2006.01) |
| *A61K 8/891* | (2006.01) |
| *A61K 8/02* | (2006.01) |
| *A61Q 1/12* | (2006.01) |
| *A61Q 17/04* | (2006.01) |
| *C08G 77/12* | (2006.01) |
| *C08G 77/20* | (2006.01) |

(52) U.S. Cl.
CPC .............. *A61Q 1/02* (2013.01); *A61K 8/0241* (2013.01); *A61K 8/86* (2013.01); *A61K 8/891* (2013.01); *A61Q 19/00* (2013.01); *C08L 83/04* (2013.01); *C08L 83/14* (2013.01); *A61K 2800/412* (2013.01); *A61K 2800/56* (2013.01); *A61K 2800/614* (2013.01); *A61K 2800/654* (2013.01); *A61Q 1/12* (2013.01); *A61Q 17/04* (2013.01); *C08G 77/12* (2013.01); *C08G 77/20* (2013.01)

(58) Field of Classification Search
None
See application file for complete search history.

(56) References Cited

U.S. PATENT DOCUMENTS

| | | | |
|---|---|---|---|
| 4,742,142 A | 5/1988 | Shimizu et al. | |
| 4,761,454 A | 8/1988 | Oba et al. | |
| 4,847,068 A * | 7/1989 | Dole | A61K 8/046 424/47 |
| 5,582,885 A * | 12/1996 | Nakamura | C08G 77/34 428/35.8 |
| 2004/0171699 A1 | 9/2004 | Morita et al. | |
| 2009/0047226 A1* | 2/2009 | Teckenbrock | A61K 8/062 424/59 |
| 2013/0095324 A1* | 4/2013 | Inokuchi | C08J 3/126 428/405 |

FOREIGN PATENT DOCUMENTS

| | | |
|---|---|---|
| JP | 62243621 A | 10/1987 |
| JP | 62-257939 A | 11/1987 |
| JP | 11-140191 A | 5/1999 |
| JP | 11-293111 A | 10/1999 |
| JP | 2002-235004 A | 8/2002 |
| JP | 2002-348475 A | 12/2002 |
| JP | 2003-12929 A | 1/2003 |
| JP | 2003-183501 A | 7/2003 |

* cited by examiner

*Primary Examiner* — Robert A Wax
*Assistant Examiner* — Quanglong Truong
(74) *Attorney, Agent, or Firm* — Birch, Stewart, Kolasch & Birch, LLP

(57) ABSTRACT

One of the purposes of the present invention is to provide an aqueous dispersion of silicone elastomer particles to provide a stable emulsion and the silicone elastomer particle, wherein a polyoxyethylene alkyl ether which has an alkyl group having a large number of carbon atoms is used as a surfactant. Further, another purpose is to provide a cosmetic comprising said aqueous dispersion or said silicone elastomer particles and giving a good feeling in the use. The present invention provides an aqueous dispersion comprising (A) silicone elastomer particles having a 90% volume cumulative diameter (D90) of 0.3 to 20 μm in an amount of 5 to 80 mass %, based on a total mass of the aqueous dispersion, (B) at least one polyoxyethylene alkyl ether having an alkyl group having 18 carbon atoms in an amount of 0.01 to 15 mass %, based on a total mass of the aqueous dispersion, wherein a hydrophile-lipophile balance (HLB) of the polyoxyethylene alkyl ether is 12.8 to 15.1, and (C) water in an amount of 19 to 94 mass %, based on a total mass of the aqueous dispersion. Further, the present invention provides a material comprising the aforesaid components (A) and (B), a method for preparing the material and a cosmetic comprising the aqueous dispersion or the material.

14 Claims, No Drawings

AQUEOUS DISPERSION COMPRISING SILICONE ELASTOMER PARTICLES, A SILICONE ELASTOMER PARTICLE AND A COSMETIC

CROSS REFERENCE

This application claims the benefits of Japanese Patent application No. 2013-224417 filed on Oct. 29, 2013, the contents of which are incorporated by reference.

The present invention relates to an aqueous dispersion comprising silicone elastomer particles, the silicone elastomer particle and a cosmetic comprising them.

BACKGROUND OF THE INVENTION

Silicone elastomer particles have been used for purposes of providing a smooth or soft feeling to cosmetics, providing a natural finish of cosmetics by scattering light, concealing pores of skin and wrinkles and thickening or stabilizing an oil phase by absorbing oil. Examples of the cosmetics include makeup cosmetics such as foundations and makeup bases, base cosmetics such as creams and milky lotions, and sunscreen cosmetics and cleansing cosmetics.

Silicone elastomer particles can be easily added to aqueous cosmetics or oil-in-water type cosmetics by the use of an aqueous dispersion of the silicone elastomer particles. However, water resistance is often needed for cosmetics such as foundations, sunscreen cosmetics, makeup bases and concealers and, therefore, silicone elastomer particles need to be added in non-aqueous type or water-in-oil type cosmetics. In this case, it is known that the silicone elastomer particles are added in a form of powder.

Japanese Patent Application Laid-Open No. Sho-62-243621 (Patent Literature 1) describes a method of dispersing a curable silicone oil in water with a surfactant and curing it to prepare an aqueous dispersion of silicone elastomer particles and, then, removing water to obtain spheric silicone elastomer particles. Japanese Patent Application Laid-Open No. Sho-62-257939 (Patent Literature 2) describes a method of spray drying an aqueous dispersion of silicone elastomer particles comprising a surfactant to obtain silicone elastomer particles. According to this method, spheric silicone elastomer particles having a low tendency for agglomeration can be easily obtained.

A surfactant used for the preparation of an aqueous dispersion of silicone elastomer particles needs to have a high emulsifying ability. Therefore, a polyoxyethylene alkyl phenyl ether with an alkyl group having 8 to 9 carbon atoms or a polyoxyethylene alkyl ether with an alkyl group having 12 to 13 carbon atoms are usually used. For instance, the surfactant, a polyoxyethylene alkyl ether, in Patent Literature 1 has an alkyl group having 12 carbon atoms. Further, a polyoxyethylene alkyl phenyl ether in Patent Literature 2 has an alkyl group having 8 carbon atoms. Japanese Patent Application Laid-Open No. Hei-11-293111 (Patent Literature 3) describes an aqueous dispersion of silicone elastomer particles, comprising a polyoxyethylene alkylether, where at least 10 weight of the alkyl groups in the polyoxyethylene alkylether has 13 carbon atoms and, therefore, a suspension of cured silicone granules having a narrow particle size distribution is provided with a small amount of a surfactant.

Use of an ionic surfactant was proposed. For instance, Japanese Patent Application Laid-Open No. Hei 11-140191 (Patent Literature 4) describes that an aqueous dispersion of silicone elastomer particles comprising both of a nonionic surfactant and an ionic surfactant improves its storage stability. Japanese Patent Application Laid-Open No. 2002-235004 (Patent Literature 5) describes that an aqueous dispersion of silicone elastomer particles comprising an amphoteric surfactant with an alkyl group having 11 to 17 carbon atoms improves its dispersibility in cosmetics.

However, polyoxyethylene alkyl phenyl ethers have such a problem that their decomposition products have the endocrine disturbance and, therefore, are being to be avoided in cosmetics. Ionic surfactants cause strong irritation on a skin, and, therefore, are being to be avoided in cosmetics which stay on skin for a long time, such as, in particular, basic cosmetics, makeup cosmetics and sunscreen cosmetics. Further, polyoxyethylene alkyl ethers with a smaller number of carbon atoms in alkyl groups cause irritation on a skin, and, therefore, are avoided sometimes in cosmetics.

Japanese Patent Application Laid-Open No. 2003-12929 (Patent Literature 6) describes an aqueous dispersion of silicone elastomer particles, comprising polyoxyethylene sorbitan monolaurate. Sorbitan fatty acid ester type surfactants have low irritation on a skin, but have less ability for emulsifying curable silicone oils.

Japanese Patent Application Laid-Open No. 2003-183501 (Patent Literature 7) describes an aqueous dispersion of silicone elastomer particles, comprising polyoxyethylene alkylether with an alkyl group having 16 carbon atoms, and that the use of an adduct of an oxyethylene to an alcohol having 16 carbon atoms as a surfactant, can provide an emulsion which has good stability and less bad influence to a human body, and offer good dispersibility for cosmetics.

PRIOR LITERATURES

Patent Literatures

[Paten Literature 1] Japanese Patent Application Laid-Open No. Sho-62-243621
[Paten Literature 2] Japanese Patent Application Laid-Open No. Sho-62-257939
[Paten Literature 3] Japanese Patent Application Laid-Open No. Hei-11-293111
[Paten Literature 4] Japanese Patent Application Laid-Open No. Hei-11-140191
[Paten Literature 5] Japanese Patent Application Laid-Open No. 2002-235004
[Paten Literature 6] Japanese Patent Application Laid-Open No. 2003-12929
[Paten Literature 7] Japanese Patent Application Laid-Open No. 2003-183501

SUMMARY OF THE INVENTION

Problems to be Solved by the Invention

As stated in the aforesaid paragraphs, when the number of carbon atoms in the alkyl group in the polyoxyethylene alkyl ether is larger, irritation on a skin is less. Then, the present inventors tried an polyoxyethylene alkyl ether which has an alkyl group having much more carbon atoms as a surfactant. However, the polyoxyethylene alkyl ether with the alkyl group having much more carbon atoms shows weaker emulsifying ability for curable silicone oils and, therefore, cannot attain enough emulsification, resulting in a broader particle size distribution. Further, when such silicone elastomer particles are added in a cosmetic, feeling in the use and spreadability tend to be bad.

One of the purposes of the present invention is to provide an aqueous dispersion of silicone elastomer particles to provide a stable emulsion and the silicone elastomer particle, wherein a polyoxyethylene alkyl ether which has an alkyl group having a large number of carbon atoms is used as a surfactant. Further, another purpose is to provide a cosmetic comprising said aqueous dispersion or said silicone elastomer particles and giving a good feeling in the use.

Means to Solve the Problems

The present inventors have made research to solve the afore-mentioned problems and found that the specific range of a hydrophile-lipophile balance (HLB) of a polyoxyethylene alkyl ether which has an alkyl group having 18 carbon atoms provides an aqueous dispersion of silicone elastomer particles having good stability.

Thus, the present invention provides an aqueous dispersion comprising (A) silicone elastomer particles having a 90% volume cumulative diameter (D90) of 0.3 to 20 μm in an amount of 5 to 80 mass %, based on a total mass of the aqueous dispersion, (B) at least one polyoxyethylene alkyl ether having an alkyl group having 18 carbon atoms in an amount of 0.01 to 15 mass %, based on a total mass of the aqueous dispersion, wherein a hydrophile-lipophile balance (HLB) of the polyoxyethylene alkyl ether is 12.8 to 15.1, and (C) water in an amount of 19 to 94 mass %, based on a total mass of the aqueous dispersion.

Further, the present invention provides a material, hereinafter referred to as "a silicone elastomer hybrid", comprising (A) silicone elastomer particles having a 90% volume cumulative diameter (D90) of 0.3 to 20 μm and (B) at least one polyoxyethylene alkyl ether attached to a surface of said component (A), wherein the polyoxyethylene alkyl ether has an alkyl group having 18 carbon atoms and a hydrophile-lipophile balance (HLB) of 12.8 to 15.1, and a method for preparing the aforesaid product.

The alkyl group of the polyoxyethylene alkyl ether contained in the present aqueous dispersion and in the silicone elastomer hybrid has more carbon atoms, compared to the conventional surfactants used in an aqueous dispersion of silicone elastomer particles. Therefore, irritation on a skin decreases. Further, the present invention provides an aqueous dispersion having good stability. A cosmetic comprising the present aqueous dispersion or the present silicone elastomer particle gives a good feeling in the use.

DETAILED DESCRIPTION OF THE INVENTION

The present invention will be described below in detail.
[Dispersion of Silicone Elastomer Particles]

The first aspect of the present invention is an aqueous dispersion comprising (A) silicone elastomer particles, (B) polyoxyethylene alkyl ether and (C) water.
(A) Silicone Elastomer Particle The shape of the silicone elastomer particle is not limited, but preferably spherical. The term "spherical" means not only that the particle is of exact sphere, but also that the particle may be of a deformed sphere whose aspect ratio, i.e. ratio of a longest diameter to a shortest diameter, is usually, on average, 1 to 4, preferably 1 to 2, more preferably 1 to 1.6, further preferably 1 to 1.4. As described below, in the case where a silicone elastomer particle is prepared by emulsifying a liquid silicone in water with a surfactant and, then, curing the liquid silicone, a shape of the particle obtained is spherical. In the case of the aqueous dispersion of the silicone elastomer particles with a particle diameter of approximately 1 μm or more, the shape of the silicone elastomer particle can be confirmed by observation with an optical microscope. In the other case where the particle diameter of the particle in the aqueous dispersion is less than 1 μm, water is removed and, then, the shape of the silicone elastomer particle can be confirmed by observation with an electron microscope.

The silicone elastomer particles have a 90% volume cumulative diameter (D90) of 0.3 to 20 preferably 3 to 15 μm. If the 90% volume cumulative diameter (D90) is larger than the aforesaid upper limit, smooth feeling of cosmetics decreases, rough feeling causes, and light scattering decreases. The silicone elastomer particles have preferably a volume-average particle diameter of 0.2 to 15 further preferably 1 to 10 μm, particularly 2 to 9 μm. If the volume-average particle diameter is less than the aforesaid lower limit, smooth feeling and light scattering are not provided sufficiently to cosmetics. If the volume-average particle diameter is larger than the aforesaid upper limit, smooth feeling of cosmetics decreases, rough feeling causes, and light scattering decreases. A method for determining a volume-average particle diameter and a 90% volume cumulative diameter (D90) are selected depending on a particle diameter of the silicone elastomer particles. When the particle diameter is approximately 1 μm or more, an electric resistance method is used. When the particle diameter is less than approximately 1 μm, a laser diffraction-scattering method is used.

The silicone elastomer particle is preferably non-sticky and has a rubber hardness of 5 to 90, more preferably 10 to 80, as determined with a Type A durometer in accordance with the Japanese Industrial Standards (JIS) K 6253. If the rubber hardness is less than the aforesaid lower limit, smooth feeling of cosmetics decreases. If the rubber hardness is larger than the aforesaid upper limit, soft feeling of cosmetics tends to decrease.

The silicone elastomer particle is preferably a cured product comprising a linear organosiloxane block represented by the formula —$(R^1_2SiO_{2/2})_n$—, wherein $R^1$ is a substituted or unsubstituted monovalent hydrocarbon group having 1 to 30 carbon atoms and n is a positive integer of from 5 to 5,000.

Examples of $R^1$ include alkyl groups such as a methyl group, an ethyl group, a propyl group, a butyl group, a pentyl group, a hexyl group, a heptyl group, an octyl group, a decyl group, an undecyl group, a dodecyl group, a tetradecyl group, a pentadecyl group, a hexadecyl group, a heptadecyl group, an octadecyl group, a nonadecyl group, an eicosyl group, a henicosyl group, a docosyl group, a tricosyl group, a tetracyl group, and a triacontyl group; aryl groups such as a phenyl group, a tolyl group, and a naphthyl group; aralkyl groups such as a benzyl group and a phenethyl group; alkenyl groups such as a vinyl group and an allyl group; cycloalkyl groups such as a cyclopentyl group, a cyclohexyl group, and a cycloheptyl group; and those hydrocarbon groups wherein a part or all of the hydrogen atoms bonded to the carbon atoms of these groups are substituted with a substituent such as halogen atoms such as a fluorine atom, a chlorine atom, a bromine atom and an iodine atom and/or with an acryloyloxy group, a methacryloyloxy group, an epoxy group, a glycidoxy group and a carboxyl group.

The silicone elastomer particle is obtained by curing a curable liquid silicone, and has a cross-linking structure, i.e. three dimension network structure. A method of curing a curable liquid silicone to obtain a silicone elastomer particle may be any conventional one. For instance, an organo(poly)siloxane having monovalent olefinically unsaturated groups each bonded to a silicon atom such as a vinyl silyl group ($\equiv$SiCH=CH$_2$) is addition reacted with an organo(poly)siloxane having hydrogen atoms each bonded to a silicon atom, i.e. hydrosilyl group ($\equiv$SiH).

A silicone elastomer particle can be prepared by an addition reaction of a liquid silicone mixture comprising an organo(poly)siloxane which is represented by an average formula: $R^2_aR^3_bSiO_{(4-a-b)/2}$ and has at least two monovalent olefinically unsaturated groups per molecule and an organohydrogen(poly)siloxane which is represented by an average formula: $R^4_cH_dSiO_{(4-c-d)/2}$ and has at least three hydrogen atoms each bonded to a silicone atom, hereinafter referred to as SiH group, per molecule. A silicone elastomer particle can also be prepared by an addition reaction of a liquid silicone mixture comprising an organo(poly)siloxane which is represented by an average formula: $R^2_aR^3_bSiO_{(4-a-b)/2}$ and has at least three monovalent olefinically unsaturated groups per molecule and an organohydrogen(poly)siloxane which is represented by an average formula: $R^4_cH_dSiO_{(4-c-d)/2}$ and has at least two SiH groups per molecule. Amounts of the organo(poly)siloxane having monovalent olefinically unsaturated groups and the organohydrogen(poly)siloxane is such that the number of the SiH group is 0.5 to 2, relative to the number of the monovalent olefinically unsaturated group.

In the aforesaid formula, $R^2$ is a substituted or unsubstituted monovalent hydrocarbon group having 1 to 30 carbon atoms except unsaturated aliphatic groups. $R^3$ is a monovalent olefinically unsaturated group having 2 to 6 carbon atoms. "a" and "b" are positive numbers satisfying the (in)equations, 0<a<3, 0<b<=3 and 0.1<=a+b<=3, preferably 0<a<=2.295, 0.005<=b<=2.3 and 0.5<=a+b<=2.3. $R^4$ is a substituted or unsubstituted monovalent hydrocarbon group having 1 to 30 carbon atoms except unsaturated aliphatic groups. "c" and "d" are positive numbers satisfying the (in)equations, 0<c<3, 0<d<=3 and 0.1<=c+d<=3, preferably 0<c<=2.295, 0.005<=d<=2.3 and 0.5<=c+d<=2.3.

Examples of $R^2$ include an alkyl group such as a methyl group, an ethyl group, a propyl group, a butyl group, a pentyl group, a hexyl group, a heptyl group, an octyl group, a decyl group, an undecyl group, a dodecyl group, a tetradecyl group, a pentadecyl group, a hexadecyl group, a heptadecyl group, an octadecyl group, a nonadecyl group, an eicosyl group, a henicosyl group, a docosyl group, a tricosyl group, a tetracyl group and a triacontyl group; an aryl group such as a phenyl group, a tolyl group and a naphthyl group; an aralkyl group such as a benzyl group and a phenethyl group; a cycloalkyl group such as a cyclopentyl group, a cyclohexyl group and a cycloheptyl group; and those hydrocarbon groups wherein a part or all of the hydrogen atoms bonded to a carbon atom of these groups is substituted with a substituent such as a halogen atom such as a fluorine atom, a chlorine atom, a bromine atom and an iodine atom and/or an acryloyloxy group, a methacryloyloxy group, an epoxy group, a glycidoxy group and a carboxyl group. Particularly, it is industrially preferable that 50 mole % or more of $R^2$ is a methyl group.

Examples of $R^3$ include a vinyl group, an allyl group, a propenyl group, a butenyl group, a pentenyl group and a hexenyl group. Particularly, a vinyl group is industrially preferable.

Examples of $R^4$ include the same groups as those described for $R^2$ above.

The organo(poly)siloxane and the organohydrogen(poly)siloxane preferably have a dynamic viscosity at 25 degrees C. of 100,000 mm$^2$/s or less, more preferably 10,000 mm$^2$/s or less. If the dynamic viscosity is higher than the aforesaid upper limit, it is difficult to obtain particles having a narrow particle size distribution in the present method described below. The organo(poly)siloxane and the organohydrogen(poly)siloxane may have a linear, cyclic or branched structure. Particularly, a linear structure is preferable. The dynamic viscosity in the present invention is determined with an Ostwald viscometer.

In the aforesaid liquid silicone mixture, it is preferred that at least three monovalent olefinic unsaturated aliphatic groups are present in the organo(poly)siloxane and/or at least three hydrosilyl groups are present in the organohydrogen(poly)siloxane. Otherwise, a cured elastomer tends to be sticky.

The platinum group metal catalyst may be any well-known or known catalyst for hydrosilylation. Examples of the catalyst include an element of platinum group metals such as platinum, including platinum black, rhodium and palladium; platinum chloride such as H$_2$PtCl$_4$.kH$_2$O, H$_2$PtCl$_6$.kH$_2$O, NaHPtCl$_6$.kH$_2$O, KHPtCl$_6$.kH$_2$O, Na$_2$PtCl$_6$.kH$_2$O, K$_2$PtCl$_4$.kH$_2$O, PtCl$_4$.kH$_2$O, PtCl$_2$, and Na$_2$HPtCl$_4$.kH$_2$O, wherein "k" is an integer of 0 to 6, preferably 0 or 6; a chloroplatinic acid and a chloroplatinate; an alcohol-modified chloroplatinic acid (see U.S. Pat. No. 3,220,972); a complex of chloroplatinic acid with an olefin (see U.S. Pat. No. 3,159,601, U.S. Pat. No. 3,159,662, and U.S. Pat. No. 3,775,452); a platinum group metal, such as platinum black and palladium, supported on a carrier such as alumina, silica and carbon; a rhodium-olefin complex; chlorotris(triphenylphosphine) rhodium (Wilkinson catalyst); and a complex of platinum chloride, chloroplatinic acid or chloroplatinate with siloxane having a vinyl group, in particular vinyl group-containing cyclic siloxane.

The amount of the platinum group metal catalyst may be an effective amount to promote a hydrosilylation. If the amount of the catalyst is too large, a polyether moiety of the surfactant is oxidized and odor may occur. The amount of the catalyst is usually such that the amount of the platinum group metal in the catalyst is 0.1 to 100 ppm by mass, preferably 0.5 to 50 ppm by mass, more preferably 1 to 30 ppm by mass, relative to a total mass of the liquid silicone mixture.

The present silicone elastomer particle may be prepared by reacting a liquid silicone mixture of an organo(poly)siloxane represented by the following formula:

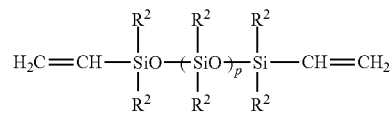

wherein p is a number such that the organo(poly)siloxane has a dynamic viscosity at 25 degrees C. of 100,000 mm$^2$/s or less, more preferably 10,000 mm$^2$/s or less, and $R^2$ is, independently of each other, as described above, and an organohydrogen(poly)siloxane represented by the following formula:

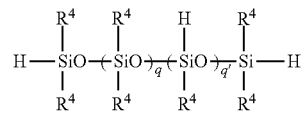

wherein q and q' are numbers such that the organohydrogen(poly)siloxane has a dynamic viscosity at 25 degrees C. of 100,000 mm²/s or less, more preferably 10,000 mm²/s or less, q' is not zero, and $R^4$ is, independently of each other, as described above,
in the presence of the aforesaid platinum group metal catalyst.

Alternatively, the silicone elastomer particle may be prepared by reacting a liquid silicone mixture of
an organo(poly)siloxane represented by the following formula:

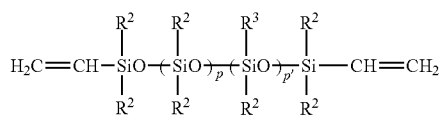

wherein p and p' are numbers such that the organo(poly)siloxane has a dynamic viscosity at 25 degrees C. of 100,000 mm²/s or less, more preferably 10,000 mm²/s or less, p' is not zero, and $R^2$ and $R^3$ are, independently of each other, as described above, and
an organohydrogen(poly)siloxane represented by the following formula:

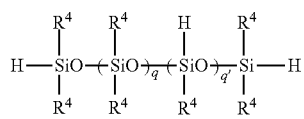

wherein q and q' are numbers such that the organohydrogen(poly)siloxane has a dynamic viscosity at 25 degrees C. of 100,000 mm²/s or less, more preferably 10,000 mm²/s or less, and $R^4$ is, independently of each other, as described above, in the presence of the aforesaid platinum group metal catalyst.

The present silicone elastomer particle may further contain a silicone oil, an organosilane, an inorganic powder and an organic powder. Amounts of those may be such as in conventional silicone elastomer particles.

The present silicone elastomer particle may contain an antioxidant in order to prevent oxidation of the components (B) and (D) described below. Examples of the antioxidant include tocophelol, p-t-buthylphenol, butylhydroxyanisol, dibutylhydroxytoluene, pentaerythritol tetrakis(3,5-di-tert-butyl-4-hydroxyhydrocinnamate) and ethoxyquin.

An amount of the silicone elastomer particles in the aqueous dispersion is preferably 5 to 80 mass %, preferably 20 to 70 mass %, further preferably 40 to 60 mass %, relative to a total mass of the aqueous dispersion. If the amount of the silicone elastomer particles is less than the aforesaid lower limit, productivity of an aqueous dispersion relative to the amount of the silicone elastomer particle is small, so that a larger amount of the aqueous dispersion needs to be added to cosmetics, which is inefficient. If the amount of the silicone elastomer particles is larger than the aforesaid upper limit, a viscosity of the aqueous dispersion is too high, so that its handling is difficult.

(B) Polyoxyethylene Alkyl Ether

The polyoxyethylene alkyl ether works as a dispersant for the silicone elastomer particles in the aqueous dispersion and cosmetics. As will described below, the polyoxyethylene alkyl ether works also as an emulsifier for the liquid silicone in the preparation of the aqueous dispersion of the silicone elastomer particles. The present polyoxyethylene alkyl ether has an alkyl group having 18 carbon atoms. If the number of the carbon atoms is smaller than 18, irritation on a skin is stronger. If the number of the carbon atoms is larger than 18, the liquid silicone may not be emulsified and it may be difficult to obtain particles having a narrow particle size distribution. Further, stability of the aqueous dispersion is worse.

In the present invention, the alkyl group in the polyoxyethylene alkyl ether may be linear or branched. The polyoxyethylene alkyl ether having a linear alkyl group is represented by the following formula (1):

$$C_{18}H_{37}O(CH_2CH_2O)_mH \qquad (1)$$

The polyoxyethylene alkyl ether having a branched alkyl group is, for instance, represented by the following formula (2):

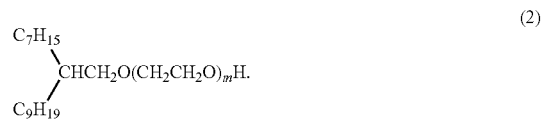

In the present invention, the polyoxyethylene alkyl ether may be used singly, or in combination of two or more of them. In the aforesaid formulas, m means the number of added ethylene oxide. m is an integer of 2 to 50, preferably 8 to 30, particularly 10 to 18. The polyoxyethylene alkyl ether may be used singly or two or more in combination of the polyoxyethylene alkyl ethers having different values of m. In particular, polyoxyethylene stearyl ether having a linear alkyl group is preferred.

In the present invention, the HLB of the polyoxyethylene alkyl ether is 12.8 to 15.1, preferably 13.2 to 14.9. If the HLB is smaller than the lower limit or larger than the upper limit, a liquid silicone may not be emulsified in a preparation process and it may be difficult to obtain particles having a narrow particle size distribution. Further, stability of an aqueous dispersion is worse. In the present invention, the HLB is calculated with the Griffin function:

HLB=[Molecular weight of a polyoxyethylene moiety/Molecular weight of polyoxyethylene alkyl ether]×20.

When the two or more polyoxyethylene alkyl ethers which have different HLB's are used in combination, the HLB is an average by mass.

The amount of the polyoxyethylene alkyl ether in the aqueous dispersion is 0.01 to 15 mass %, preferably 0.05 to 10 mass %, in particular 0.1 to 3 mass %, based on a total mass of the aqueous dispersion. If the amount is smaller than the lower limit, the liquid silicone cannot be emulsified in a preparation process and it is difficult to obtain particles having a narrow particle size distribution. Further, the stability of the aqueous dispersion is worse. Even if the amount of the polyoxyethylene alkyl ether is larger than the upper limit, the particle size of the silicone elastomer particles obtained does not become smaller any more, the water dispersity of the silicone elastomer particles is not further improved, and irritation on a skin tends to increase.

(C) Water

In the present invention, the component (C), water, works as a dispersion medium for the aforesaid (A) silicone elastomer particles. Further, the water works as a dispersion medium for a liquid silicone in a preparation process. For instance, ion-exchanged water may be used. The amount of water is 19 to 94 mass %, preferably 30 to 80 mass %, based on a total amount of the aqueous dispersion.

(D) Polyoxyethylene Sorbitan Monostearate and Polyoxyethylene Sorbitan Tristearate Polyoxyethylene sorbitan monostearate and polyoxyethylene sorbitan tristearate are used as a dispersion medium for a platinum group metal catalyst, as will described in the preparation of the silicone elastomer particles. Although the polyoxyethylene alkyl ether (B) may be used as a dispersion medium for a platinum group metal catalyst, polyoxyethylene sorbitan monostearate and polyoxyethylene sorbitan tristearate are preferred because of its good solubility to a solvent for the platinum group metal catalyst. In particular, polyoxyethylene sorbitan tristearate is preferred.

The stearyl groups of the polyoxyethylene sorbitan monostearate and polyoxyethylene sorbitan tristearate may be linear or branched, and a number of added ethylene oxide is 2 to 50. These components may be used singly, in combination of two or more of them having a different number of added ethylene oxide. Examples of the polyoxyethylene sorbitan monostearate include a polyoxyethylene sorbitan monostearate with 6 or 20 oxyethylene, and polyoxyethylene sorbitan monoisostearate with 20 oxyethylene. Examples of the polyoxyethylene sorbitan tristearate include polyoxyethylene sorbitan tristearate with 6 or 20 oxyethylene and polyoxyethylene sorbitan triisostearate with 20 oxyethylene. The component may be used singly, or in combination of two or more of them having a different number of added ethylene oxide. The amount of the component (D) is 0.01 to 10 mass %, preferably 0.05 to 5 mass %, based on a total amount of the aqueous dispersion.

Other Components

The aqueous dispersion of the silicone elastomer particles may contain a water-soluble polymer in order to increase the dispersibility of the particles. Examples of the water-soluble polymer include nonionic water-soluble polymers, anionic water-soluble polymers, cationic water-soluble polymers and amphoteric water-soluble polymers, but are not limited to these. In particular, nonionic water-soluble polymers are preferred.

Examples of the nonionic water-soluble polymer include a copolymer of vinylalcohol and vinyl acetate, a polymer of acrylamide, a polymer of vinyl pyrrolidone, a copolymer of vinyl pyrrolidone and vinyl acetate, polyethyleneglycol, a polymer of isopropylacrylamide, a polymer of methyl vinyl ether, starch, methyl cellulose, hydroxyethyl cellulose, hydroxypropyl cellulose, guar gum and xanthan gum.

Examples of the anionic water-soluble polymer include a polymer of sodium acrylate, a copolymer of sodium acrylate and sodium maleate, a copolymer of sodium acrylate and acrylamide, a polymer of styrenesulfonic acid sodium, a copolymer of polyisoprene surfonic acid sodium and styrene, a polymer of sodium naphthalenesulfonate, carboxymethylstarch, starch phosphate, carboxymethyl cellulose, sodium alginate, gum arabic, carrageenan, sodium chondroitin sulfate and sodium hyaluronate.

Example of the cationic water-soluble polymer include a polymer of dimethyl diallyl ammonium chloride, a polymer of vinyl imidazoline, a polymer of methyl vinyl imidazolium chloride, a polymer of ethyl acrylate trimethyl ammonium chloride, a polymer of ethyl methacrylate trimethyl ammonium chloride, a polymer of (3-acrylamidopropyl)trimethylammonium chloride, a polymer of (3-methacrylamidepropyl)trimethylammonium chloride, a copolymer of epichlorohydrin and dimethylamine, a polymer of ethylene imine, a quaternary compound of polyethylene imine, a polymer of allylamine hydrochloride salt, polylysine, cationic starch, cationic cellulose, chitosan, and these substances copolymerized with a monomer containing a nonionic group or an anionic group.

Examples of the amphoteric water-soluble polymer include a copolymer of ethyl acrylate trimethyl ammonium chloride, acrylic acid and acrylamide; a copolymer of ethyl methacrylate trimethyl ammonium chloride, acrylic acid and acrylamide; and Hofmann degradation product of a polymer of acrylamide.

The present aqueous dispersion may contain antibacterial preservatives and antimicrobial agents. Examples of the antibacterial preservatives include p-hydroxybenzoic acid alkyl ester, benzoic acid, sodium benzoate, sorbic acid, potassium sorbate and phenoxy ethanol. Examples of the antimicrobial agents include benzoic acid, salicylic acid, carbolic acid, sorbic acid, p-hydroxybenzoic acid alkyl ester, p-chlorometacresol, hexachlorophene, benzalkonium chloride, chlorhexidine chloride, trichlorocarbanilide, a photosensitive element and phenoxy ethanol.

[Method for Preparing the Aqueous Dispersion of Silicone Elastomer Particles]

The aqueous dispersion of silicone elastomer particles may be prepared by the steps of adding (B) polyoxyethylene alkyl ether and (C) water to the aforesaid curable liquid silicone, stirring the mixture to emulsify and, then, adding a platinum group metal catalyst and, if needed, component (D) thereto, and further stirring to cure the curable liquid silicone.

The silicone elastomer particles in the aqueous dispersion have a 90% volume cumulative diameter (D90) of 0.3 to 20 μm, preferably 3 to 15 μm. When the 90% volume cumulative diameter (D90) is in the aforesaid range, a cosmetic gives good feeling in the use such as smooth feeling and no rough feeling. The silicone elastomer particles in the aqueous dispersion preferably have a volume-average particle diameter of 0.2 to 15 μm, further preferably 2 to 10 μm. The aforesaid particle diameter can be attained by properly controlling the amount of the polyoxyethylene alkyl ether having the specific HLB and the amount of water added in the emulsification step, depending on a manner of the emulsification. For instance, when emulsification is carried out with a homomixer and the amount of the polyoxyethylene alkyl ether added in an emulsification step is larger or the amount of water initially added in an emulsification step is smaller, the particle diameter tends to be smaller. When the stirring speed is faster, the particle diameter tends to be smaller.

It is desired to incorporate an silicone oil, an organosilane, inorganic fillers, organic fillers or an antioxidant in the silicone elastomer particle, these materials may be mixed with the curable liquid silicone in advance. The amounts of these materials may be properly selected so that the volume-average particle diameter and the 90% volume cumulative diameter (D90) of silicone elastomer particles are in the aforesaid ranges.

The emulsification may be conducted with a conventional emulsification and dispersion apparatus. Examples of the emulsification and dispersion apparatus include a high-speed rotation and centrifugal dispersion type agitator such as a homodisper; a high-speed rotation and shearing type agitator such as a homomixer; a high-pressure injection-type emulsification disperser such as a homogenizer; a colloid mill; and an ultrasonic emulsifier.

The platinum group metal catalyst may be those described above. The platinum group metal catalyst may be added to an emulsion of the liquid silicone mixture or dissolved in the liquid silicone mixture in advance, as mentioned above. In the former case, the platinum group metal catalyst may be dissolved in a solvent and added. When the dispersibility of the catalyst in water is poor, it is preferable that the catalyst is dissolved in (D) polyoxyethylene sorbitan monostearate or polyoxyethylene sorbitan tristearate and added to the emulsion. In the case where the platinum group metal catalyst is dissolved in the liquid silicone mixture in advance, it is better to cool the mixture to a low temperature such as 5 degrees C. or below so as to prevent curing until the end of the emulsification. The curing reaction of the liquid silicone may be conducted at a normal temperature, such as 15 to 20 degrees C. If the reaction is not complete, the curing may be conducted under heating at a temperature below 100 degrees C. The stirring time for the curing reaction is not particularly limited and is usually 1 to 24 hours.

[Silicone Elastomer Hybrid]

The present invention further provides a material, hereinafter refer to as "a silicone elastomer hybrid", which comprises (A) silicone elastomer particle and (B) polyoxyethylene alkyl ether which attaches to the surface of component (A). The silicone elastomer hybrid is in the particle form, and is obtained by removing water from the aqueous dispersion obtained in the afore-mentioned methods. The amount of the polyoxyethylene alkyl ether is 0.1 to 20 parts by mass, preferably 0.3 to 5 parts by mass, particularly 0.5 to 2 parts by mass, relative to 100 parts by mass of the silicone elastomer particle.

Water may be removed for instance by volatilization. The volatilization may be carried out with heating under a normal pressure or a reduced pressure. In this step, (B) polyoxyethylene alkyl ether remains on and attaches to the surface of (A) silicone elastomer particle. When (D) polyoxyethylene sorbitan monostearate or polyoxyethylene sorbitan tristearate is used as a dispersion medium for a platinum group metal catalyst, component (D) also remains on and attaches to the surface of the silicone elastomer particle.

Specifically, water is removed, for instance, by heating the dispersion standing still, heating the dispersion under stirring, spraying the dispersion in hot air stream in a spray dryer, or using a fluid heating medium. The dispersion may be concentrated, for instance, by centrifugalization or decantation, as pre-treatment before the afore-mentioned step. A salt or an alcohol may be added to the dispersion to break the dispersion state and, then, the resulting materials are be concentrated by filtration, centrifugalization or decantation.

When all of the water is removed by a volatilization, the components (A), (B) and (D), which are not volatile, remain in the silicone elastomer hybrid, while maintaining their initial ratios. Therefore, the amount of the component (B) relative to the amount of the component (A) in the silicone elastomer hybrid obtained is same as that in the aqueous dispersion. In a case where the aqueous dispersion contained the component (D), the amount of the component (D) relative to the amount of the component (A) in the silicone elastomer hybrid is also same as that in the aqueous dispersion. When the aqueous dispersion was concentrated by centrifugation or decantation, the components (B) and (D) dissolved in water and, therefore, the ratios of the components (B) and (D) relative to the component (A) in the silicone elastomer hybrid are different from the initial ratios.

In the present invention, preferred is a method for spraying the dispersion in hot air stream, i.e. a spray and drying method, to remove water, because strong agglomeration of the silicone elastomer hybrid particles does not occur.

[Cosmetics]

The present invention further provides a cosmetic comprising the aforesaid aqueous dispersion of the silicone elastomer particles or the aforesaid silicone elastomer hybrid.

The present aqueous dispersion and the silicone elastomer hybrid may be added to various kinds of cosmetics such as skincare cosmetics, makeup cosmetics, hair cosmetics, antiperspirant cosmetics and UV-ray protective cosmetics, particularly, cosmetics applied for a skin or hair. The amounts of the aqueous dispersion or the silicone elastomer hybrid may be selected for each cosmetic and are not limited to any particular one. In particular, the amounts of the aqueous dispersion or the silicone elastomer hybrid are such that the amount of the silicone elastomer particles is 0.1 to 50 mass %, based on a total mass of the cosmetic.

The mean particle diameter of the silicone elastomer particles is preferably 2 to 15 µm in order to improve feeling and provide effects of soft focus and concealing wrinkles and pores of skin. When the cosmetic is used to conceal wrinkles and pores of skin, a few kinds of silicone elastomer particles having different mean particle diameters may be used in combination.

The cosmetic may contain any other components which are commonly used in cosmetics, such as (E) oil agents, (F) compounds having an alcoholic hydroxide group, (G) water-soluble or -swellable polymers, (H) particles other than the aforesaid silicone elastomer particle (A), surfactants other than the aforesaid components (B) and (D), (J) compositions comprising a cross-linkable organopolysiloxane and oil which is liquid at room temperature, (K) oil-soluble film-forming agents, (L) silicone waxes, and other additives. These components may be used singly, or in combination of two or more of them.

(E) The oil agent may be solid, semisolid or liquid at room temperature. Examples of the oil agent include natural animal or plant oils, semisynthetic oils, hydrocarbon oils, higher alcohols, ester oils, silicone oils and fluorized oils.

Examples of the natural animal or plant oils and the semisynthetic oils include avocado oil, olive oil, carnauba wax, liver oil, candelilla wax, purified candelilla wax, hardened oil, wheat germ oil, sesame oil, rice germ oil, rice bran oil, sugar cane oil, sasanqua oil, safflower oil, shear butter, jojoba oil, hydrogenated jojoba oil, squalane oil, camellia oil, evening primrose oil, corn oil, rapeseed oil, rice bran wax, germ oil, palm oil, palm kernel oil, hardened castor oil, sunflower oil, macadamia nut oil, beeswax, meadowfoam oil, cottonseed oil, japanese wax, coconut oil, hardened coconut oil, tri-coconut oil fatty acid glyceride and peanut oil.

The hydrocarbon oils may be linear or branched and may be volatile. Specifically, examples of the hydrocarbon oils include alfa-olefin oligomers, isoparaffin, isododecane, isohexadecane, squalane, synthetic squalane, plant-derived squalane, ceresin, paraffin, paraffin wax, polyethylene wax, polyethylene-polypropylene wax, ethylene/propylene/stylene copolymer, butylenes/propylene/stylene copolymer, liquid paraffin, pristine, polyisobutylene, hydrogenated polyisobutene, microcrystalline wax, and vaseline. Examples of higher fatty acid include lauric acid, myristic acid, palmitic acid, stearic acid, behenic acid, oleic acid, isostearic acid and 12-hydroxystearic acid.

Examples of the higher alcohols include myristyl alcohol, palmityl alcohol, stearyl alcohol, behenyl alcohol, oleyl alcohol, isostearyl alcohol, hexyldodecanol, octyl dodecanol, cetostearyl alcohol, 2-decyltetradecynol, cholesterol, phytosterol, batyl alcohol, and cerakyl alcohol.

Examples of the ester oils include adipic acid 2-hexyldecyl, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, neopentylglycol dioctanoate, neopentylglycol dicaprate, triethyl citrate, 2-ethylhexyl succinate, isocetyl stearate, butyl stearate, diisopropyl sebacate, bis(2-ethylhexyl) sebacate, cetyl lactate, myristyl lactate, isononyl isononate, isotridecyl isononanoate, isopropyl palmitate, 2-ethylhexyl palmitate, 2-hexyldecyl palmitate, dipentaerythritol fatty acid ester, isopropyl myristate, octyldodecyl myristate, 2-hexyldecyl myristate, myristyl myristate, 2-octyldodecyl N-lauroyl-L-glutamate, isopropyl lauroyl sarcosinate, diisostearyl malate, and glyceride oils such as acetoglyceryl, glyceryl triisooctanoate, glyceryl triisostearate, glyceryl triisopalmitate, glyceryl tribehenate, glyceryl monostearate, glyceryl di-2-heptylundecanoate, glyceryl trimyristate and diglyceryl myristate/isostearate.

Examples of the silicone oils include linear or branched organopolysiloxane having a low to high viscosity, such as dimethylpolysiloxane, caprylyl methicone, phenyl trimethicone, tetrakis(trimethylsiloxy)silane, methylphenylpolysiloxane, methylhexylpolysiloxane and dimethylsiloxane/methylphenylsiloxane copolymer; cyclic organopolysiloxanes such as octamethylcyclotetrasiloxane, decamethylcyclopentasiloxane, dodecamethylcyclohexasiloxane, tetramethyltetrahydrogencyclotetrasiloxane and tetramethyltetraphenylcyclotetrasiloxane; amino-modified organopolysiloxane, pyrrolidone-modified organopolysiloxane; silicone rubbers such as high-polymerized dimethylpolysiloxane rubber, amino-modified organopolysiloxane rubber, and dimethylsiloxane-methylphenylsiloxane-copolymer rubber; higher alkoxy-modified silicone such as stearoxy silicone, higher fatty acid-modified silicone, alkyl-modified silicone, long-chain alkyl-modified silicone, amino acid-modified silicone and fluorized silicone.

Examples of the fluorinated oils include perfluoropolyether, perfluorodecaline and perfluorooctane. The amount of the component (E) may be selected in a range of 1 to 98 mass %, based on a total mass of the cosmetic, depending on a form of the cosmetic.

(F) Examples of the compounds having an alcoholic hydroxide group include lower alcohols such as ethanol, sugar alcohols such as sorbitol and polyhydric alcohols such as glycerin, butylene glycol, dibutylene glycol and pentylene glycol. The amount of the component (F) is 0.1 to 20 parts by mass of a total amount of the cosmetic.

(G) Examples of the water-soluble or -swellable polymers include plant-derived polymers such as gum arabic, guar gum, carrageenan, agar, quince seed, starch, algae colloid, tragacanth gum and locust bean gum; microorganism-derived polymers such as xanthan gum, dextran, succinoglucan and pullulan; animal-derived polymers such as collagen, casein, albumen and gelatin; cellulose polymers such as hydroxypropyl methyl cellulose, hydroxymethyl cellulose, hydroxypropyl cellulose and sodium carboxymethyl cellulose; alginic acid polymers such as sodium alginate and propylene glycol alginate; vinyl polymers such as an (acrylates/C10-30 alkyl acrylate)crosspolymer and a carboxyvinyl polymer; acrylic polymers such as polyethylene glycol, a polyoxyethylene polyoxypropylene copolymer, sodium polyacrylate, polyacrylamide, an (ammonium acryloyldimethyltaurate/VP)copolymer, an (ammonium acryloyldimethyltaurate/beheneth-25 methacrylate)crosspolymer, a (sodium acrylate/sodium acryloyldimethyl taurate)copolymer and a (hydroxyethyl acrylate/sodium acryloyldimethyl taurate)copolymer; aqueous synthetic polymers such as a polyethyleneimine and a cationic polymer; and water-swellable inorganic minerals such as bentonite, aluminum magnesium silicate, montmorillonite, saponite and hectorite. The water-swellable polymer compounds include compounds which are used as a film-forming agent, such as polyvinyl alcohol and polyvinylpyrrolidone. The amount of component (G) is preferably 0.1 to 20 mass %, based on a total amount of the cosmetic. In an aqueous type cosmetic and an O/W emulsion type cosmetic, vinyl polymers and acryl polymers are preferred because emulsion stability and an increased viscosity are easily obtained.

(H) The particles other than the component (A) may be powders which are commonly used in cosmetics. Any particle may be used, regardless of a shape such as spherical, acicular, plate-like, dendritic, fibrous or amorphous; a size such as like smoke or fog state, moictroparticles and pigments; and particle structure such as porous, non-porous, hollow or hollow and porous. Examples of such powders include inorganic powders, coloring pigments, organic powders, metal soaps and inorganic-organic hybrid powders.

Examples of the inorganic powders include powders of magnesium oxide, barium sulfate, calcium sulfate, magnesium sulfate, calcium carbonate, magnesium carbonate, talc, cleavage talc, mica, kaolin, sericite, white mica, synthetic mica, bronze mica, lepidolite, biotite, silica, silica fine particles, aluminum silicate, magnesium silicate, aluminum magnesium silicate, calcium silicate, hydroxyapatite, zeolite, dibasic calcium phosphate, alumina, aluminium hydroxide and boron nitride.

The coloring agents may be pigments and dyes. Examples of the colorling pigments include inorganic red pigments such as iron oxide, iron hydroxide and iron titanate; inorganic bister pigments such as gamma-iron oxide; inorganic yellow pigments such as yellow iron oxide and loess; inorganic black pigments such as black iron oxide and carbon black; inorganic purple pigments such as iron pigment covered with silica, manganese violet and cobalt violet; inorganic green pigments such as chromium hydroxide, chromium oxide, cobalt oxide and cobalt titanate; inorganic blue pigments such as prussian blue and ultramarine blue; white pigments such as titanium mica, titanium mica coated with pigments and titanium oxide; pearl pigments such as synthetic bronze mica; synthetic resin powders provided by insolubilizing tar dyes or natural dyes or combining these powders. The pigments are often surface-treated with hydrophobizing agents in order to improve dispersibility in cosmetics, improve durability of makeup and increase water resistance.

Examples of the organic powders include polyamide powder, poly(acrylic acid-co-acrylate ester) powder, polyester powder, polyethylene powder, polypropylene powder, polyurethane powder, vinyl resin powder, tetrafluoro ethylene powder, polymethyl methacrylate powder such as poly (methyl methacrylate), cellulose powder, silk powder, nylon powder, polymethylsylsesquioxane powder, (vinyl dimethicone/methicone silsesquioxane) crosspolymer powder, (diphenyl dimethicone/vinyl phenyl dimethicone/silsesquioxane) crosspolymer powder, poly silicone-1 crosspolymer powder and polysilicone-22 powder. These powders are often used in combination of two or more of them because their smooth or soft feeling and oil absorption ability are different from each other.

Examples of the metal soaps include zinc stearate, aluminum stearate, calcium stearate, magnesium stearate, zinc myristate, magnesium myristate, zinc cetyl phosphate, calcium cetyl phosphate and sodium cetyl phosphate.

The inorganic-organic hybrid powders may be such obtained by surface-coating of inorganic powders, which are generally used in cosmetics, with organic powders in well-known manners.

(I) The surfactants other than components (B) and (D) may not be limited to any particular one. Any surfactants which are commonly used in cosmetics may be used. Examples of the surfactants include nonionic, anionic, cationic or amphoteric surfactants.

Among the well-known surfactants, preferred are a linear or branched organopolysiloxane having a silicone structure in the main chain and a polyoxyethylene chain, a linear or branched organopolysiloxane having a polyglycerin chain, and alkyl-comodified ones of these organopolysiloxanes. Examples of the commercial products thereof include KF-6017, KF-6028, KF-6028P, KF-6038, KF-6100, KF-6104 and KF-6105, which are available from Shin-Etsu Chemical Co., Ltd. In particular, preferred are surfactants which contain a polyoxyethylene group, a polyoxyethylene-polyoxypropylene group or a polyglycerin group of 5 to 30 mass % per molecular. The amount of the surfactant is 0.1 to 5 parts by mass of a total amount of the cosmetic.

In the compositions comprising (J) cross-linkable organopolysiloxane and oil which is liquid at room temperature, it is preferred that the cross-linkable organopolysiloxane swells, while containing an amount of the own weight or more of a liquid oil. Examples of the liquid oil include liquid silicone oils, hydrocarbon oils, ester oils, natural animal or plant oils and semisynthetic oils. In particular, use may be made of low viscosity silicone oils having a viscosity of 0.65 to 100.0 $mm^2$/s at 25 degrees C.; hydrocarbon oils such as liquid paraffin, squalane, isododecane and isohexadecane; glyceride oils such as trioctanoin; ester oils such as isotridecyl isononanoate, N-acylglutamate and N-lauroyl sarcosinate; and natural animal or plant oils such as a macadamia nut oil. It is preferred that a cross-linking structure is formed by a reaction of a compound having at least two vinyl type reactive groups and an organo(poly)siloxane having hydrogen atoms each bonding to a slicon atom. Examples of the compound having at least two vinyl type reactive groups include an organopolysiloxane having at least two vinyl groups, a polyoxyalkylene having at least two allyl groups, a polyglycerin having at least two allyl groups, and alfa, omega-alkenyl diene. Use may be made of the cross-linkable organopolysiloxane which has at least one structure selected from polyoxyalkylene structure, polyglycerin structure, long-chain alkyl structure, an alkenyl structure, an aryl structure and fluoroalkyl structure. The amount of the component (J) is preferably 0.1 to 80 mass %, further preferably 1 to 50 mass %, based on a total amount of cosmetic.

Examples of the commercial products of the component (J) include KSG-15, KSG-16, KSG-18A, KSG-1610, USG-103, KSG-210, KSG-240, KSG-710, USG-106 which is made in a paste state with hydrocarbon oils or triglyceride oils, KSG-41, KSG-42, KSG-43, KSG-44, KSG-310, KSG-320, KSG-330, KSG-340, KSG-810, KSG-820, KSG-830, and KSG-840, which are available from Shin-Etsu Chemical Co., Ltd.

Examples of (K) oil-soluble, film-forming agents include acrylsilicone resins, silicone network resins such as trylmethylsiloxy silicate, silicone modified pullulans, and silicone modified polynorbornenes. These components are used singly, or in combination of two or more of them, in order to control water resistance, oil resistance, adhesion, feeling, hardness, and dispersibility of powders. Examples of the commercial products thereof include KP-541, KP-543, KP-545, KP-549, KP-550, KP-571, KP-575, KF-7312J, TSPL-30-D5, and NBN-30-ID, which are available from Shin-Etsu Chemical Co., Ltd. The amount of the component (K) is 0.1 to 20 parts by mass of a total amount of the cosmetic.

(L) Silicone wax is preferably an acryl silicone resin having an acryl/silicone graft or block copolymer. Examples of the commercial products of the silicone wax having long chain alkyl include KP-561P and KP-562P, which are available from Shin-Etsu Chemical Co., Ltd. These products have melting points which are near to a temperature of a human skin, so that have a specific moist feeling or adherence to a skin.

The present cosmetic may be powder, in an oily form, an oil-in-water emulsion, a water-in-oil emulsion, a non-aqueous emulsion and a W/O/W type or an O/W/O type multiple emulsion. When an aqueous cosmetic with an aqueous contisuous phase or an O/W type cosmetic is prepared, an aqueous dispersion of the silicone elastomer particles may be used or the silicone elastomer hybrid may be dispersed in water with an additional surfactant. The total amount of water may be selected in the range of 40 to 90 mass %, based on a total amount of the cosmetic. When the W/O type cosmetic is prepared, the silicone elastomer hybrid is usually dispersed in an oil phase. In this case, the amount of water may be selected in the range of 0.1 to 70 mass %, based on a total amount of the cosmetic.

The present cosmetic may contain any other additives, such as oil soluble gelling agents, antiperspirant agents, ultraviolet absorbing agents, ultraviolet scattering agents, humectants, antibacterial preservatives, perfumes, salts, antioxidants, pH adjustors, chelate agents, refrigerants, anti-inflammatory agents, components for skin enrichment such as skin-whitening agents, cell activators, rough skin improvers, blood circulation accelerators, skin astringents and seborrhea inhibitors, vitamins and amino acids.

Examples of the oil soluble gelling agents include metal soaps such as aluminum stearate, magnesium steatate and zinc myristate; amino acid derivatives such as such as N-lauroyl-L-glutamic acid and alfa-gamma-di-n-butylamine; dextrin fatty esters such as dextrin palmitate, dextrin stearate and dextrin 2-ethyl hexanoate/palmitate; sucrose fatty acid esters such as sucrose palmitate, sucrose stearate; flactooligosaccharide fatty acid esters such as flactooligosaccharide stearate and flactooligosaccharide 2-etylhexanoate; organic modified clay minerals such as dimethylbenzyldodecylammonium montmorillonite clay and dimethyldioctadecyl ammonium montmorillonite clay.

Examples of the antiperspirant agents include aluminium chlorohydrate, aluminium chloride, aluminium sesquichlorohydrate, zirconyl hydroxychloride, aluminium zirconium hydroxylchloride and aluminium zirconium glycine complex.

Examples of the ultraviolet absorbing agents include benzoic acid ultraviolet absorbing agents such as 4-aminobenzoic acid; anthranilic acid ultraviolet absorbing agents such as a methyl anthranilate; salicylic acid ultraviolet absorbing agents such as a methyl salicylate, an octyl salicylate, a salicylic acid 3,3,5-trimethylcyclohexyl; cinnamic acid ultraviolet absorbing agents such as an octyl methoxycinnamate; benzophenone ultraviolet absorbing agents such as 2,4-dihydroxybenzophenone; urocanic acid ultraviolet absorbing agents such as an urocanic acid ethyl; dibenzoylmethane ultraviolet absorbing agents such as 4-tert-butyl-4'-methoxy-dibenzoylmethane; phenylbenzimidazole sulfonic acid and triazine delivatives. Examples of the ultraviolet scattering agents include particles which can absorb and scatter an ultraviolet, such as titanium oxide microparticles, iron-containing titanium oxide microparticles, zinc oxide microparticles and cerium oxide microparticles, and their composites. The aforesaid particles may be dispersed in oil in advance.

Examples of the humectants include hyaluronic acid, chondroitin sulfate, pyrrolidone carboxylic acid salt, polyoxyethylene methyl glucoside, polyoxypropylene methyl glucoside, lecithin, phosphatidylcholine, phosphatidylserine, phosphatidylglycerol, phosphatidylinositol and sphingolipid.

Examples of the antibacterial preservatives include paraben, benzoic acid, sodium benzoate, sorbic acid, potassium sorbate, phenoxyethanol, salicylic acid, benzalkonium chloride and chlorhexidine hydrochloride.

Examples of the salts include inorganic salts, organic salts, amine salts and amino acid salts. Examples of the inorganic salts include sodium salts, potassium salts, magnesium salts, calcium salts, aluminum salts, zirconium salts and zinc salts of an inorganic acid such as a hydrochloric acid, a sulfuric acid, a carbonic acid and a nitric acid. Examples of the organic salts include salts of an organic acid such as citric acid, malic acid, succinic acid and ascorbic acid. Examples of the amine salts and amino acid salts include salts of amines such as triethanolamine and salts of amino acids such as glutamic acid. Salts obtained by neutralization of an acid and an alkali, which are used in a cosmetic formulation, may be used.

Examples of the antioxidants include tocopherol, dibutylhydroxytoluene and phytic acid. Examples of the pH adjustors include lactic acid, citric acid, glycolic acid, succinic acid, DL-malic acid, potassium carbonate, sodium hydrogen carbonate and ammonium hydrogen carbonate. Examples of the chelate agents include alanine, ferric sodium edetate, sodium polyphosphate, sodium metaphosphate and phosphoric acid. Examples of the refrigerants include L-menthol and camphor. Examples of the anti-inflammatory agents include allantoin, glycyrrhizic acid and its salt, glycyrrhetinic acid and stearyl glycyrrhetinate and tranexamic acid.

Examples of the components for skin enrichment include skin-whitening agents such as a placental extract, arbutin, glutathione and a saxifraga stolonifera extract; cell activators such as royal jelly, a photosensitizer and cholesterol derivatives; rough skin improvers; blood circulation accelerators such as benzyl nicotinate, beta-butoxyethyl nicotinate, capsaicin, zingerone, tinctura cantharidis, α-borneol, tocopherol nicotinate, inositol hexanicotinate, cyclandelate, acetylcholine and gamma-oryzanol; skin astringents such as zinc oxide and tannic acid; and seborrhea inhibitors such as a sulfur and a thiane troll.

Examples of vitamins include vitamin A groups such as vitamin A oil, retinol, retinol acetate and retinol palmitate; vitamin B groups such as vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and derivatives thereof, and vitamin $B_{15}$ and derivatives thereof; vitamin C groups such as L-ascorbic acid, L-ascorbic acid dipalmitate, L-ascorbic acid-2-sulfate sodium and L-ascorbic acid phosphate diester dipotassium; vitamin D groups such as ergocalciferol and cholecalciferol; vitamin E groups such as alpha-tocopherol, beta-tocopherol, gamma-tocopherol, DL-alpha-tocopherol, DL-alpha-tocopherol nicotinate and DL-alpha-tocopherol succinate; nicotinic acid groups such as nicotinic acid, benzyl nicotinate and nicotinic acid amide; vitamin H; vitamin P; pantothenic acid groups such as pantothenate calcium, D-pantothenyl alcohol, pantothenyl ethyl ether and acetylpanthothenyl ethyl ether; and biotin.

Examples of amino acids include serine, arginine, lysine, proline, glutamic acid, cystine and cysteine.

Examples of the present cosmetic include skin care cosmetics such as lotion, milky lotion, cream, cleansing, pack, oil ligid, massage agent, cosmetic essence, cosmetic oil, cleaning agent, deodorant, hand cream, lip balm, and wrinkle-concealing cosmetic; make up cosmetics such as makeup base, concealer, white powder, powder foundation, liquid foundation, cream foundation, oily foundation, blusher, eye shadow, mascara, eyeliner, eyebrow cosmetic and rouge; hair care cosmetics such as shampoo, rinse, conditioner and hair setting agent; antiperspirant cosmetic; and ultraviolet protection cosmetics such as sunscreen oil, sunscreen milky lotion and sunscreen cream.

The cosmetic may be in various forms such as liquid, milky liquid, cream, solid, paste, gel, powder, pressed one, a multilayer structure, moose, spray, stick and pencil form, but not limited to these.

EXAMPLES

The present invention will be described in detail by referring to the Examples and the Comparative Examples below, but is not limited thereto. In the Examples and the Comparative Examples, the dynamic viscosity was determined with an Ostwald viscometer at 25 degrees C. and the abbreviation "%" means a mass percent.

Example 1

Preparation of an Aqueous Dispersion of Silicone Elastomer Particles

In one-liter glass beaker, putted were 250 g of methylvinylpolysiloxane represented by the following formula (3) and having a dynamic viscosity of 130 mm²/s,

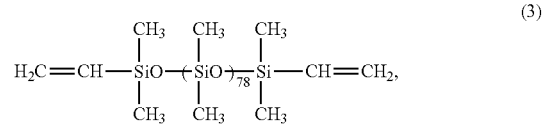

250 g of methylvinylpolysiloxane represented by the following formula (4) and having a dynamic viscosity of 600 mm²/s,

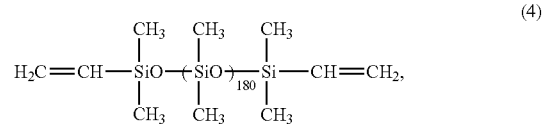

and 32 g of methylhydrogenpolysiloxane represented by the following formula (5) and having a dynamic viscosity of 30 mm²/s,

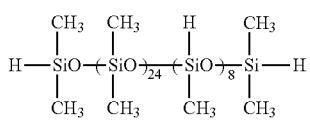

(5)

whose amount is such that the number of the hydrosilyl group is 1.11 per the total number of the olefinic unsaturated groups in the aforesaid compounds (3) and (4), and stirred and dissolve each other with a homomixer at 2,000 rpm. Subsequently, 3 g of polyoxyethylene stearyl ether with 15 moles of added ethylene oxide, hereinafter abbreviated as "EO", and an HLB of 14.3, EMALEX 615, ex Nihon Emulsion Co., Ltd., and 50 g of water were added thereto and, then, stirred with a homomixer at 8,000 rpm, whereby an oil-in-water state was obtained and thickening was observed. Then, the stirring was continued for further 15 minutes. Subsequently, 413 g of water was added thereto with stirring at 2,000 rpm to obtain a homogenous white emulsion.

This emulsion was taken in a one-liter glass flask equipped with a stirrer having anchor type stirring blades, and the temperature thereof was adjusted to 15 to 20 degrees C. Then, added with stirring was a solution consisting of 0.8 g of a solution of a chloroplatinic acid-olefin complex in isododecane, containing 0.5 mass % of platinum, and 1 g of polyoxyethylene sorbitan tristearate, NIKKOL TS-30V, ex Nikko Chemicals Co., Ltd., with 20 moles of EO. The resulting mixture was stirred for 12 hours at the same temperature to obtain an aqueous dispersion of silicone elastomer particles, hereinafter referred to as aqueous dispersion 1.

The silicone elastomer particles in the aqueous dispersion 1 thus obtained was spherical under observation with an optical microscope and had a volume-average particle diameter of 9 μm and a 90% volume cumulative diameter (D90) of 12 μm as determined with a particle size distribution measurement instrument using an electric resistance method, Multisizer 3, ex Beckman Coulter, Inc.

Rubber hardness of the silicone elastomer particles was determined according to the following method.

The methylvinylpolysiloxane represented by the afore-mentioned formula (3), the methylvinylpolysiloxane represented by the afore-mentioned formula (4), the methylhydrogenpolysiloxane represented by the afore-mentioned formula (5), and the solution of a chloroplatinic acid-olefin complex in isododecane, containing 0.5 mass % of platinum, were mixed in the same ratio as in Example 1, poured into an aluminum petri dish up to a depth of 10 mm and allowed to stand at 25 degrees C. for 24 hours. Then, the mixture was heated in a thermostat at 50 degrees C. for one hour to obtain a silicone elastomer. Rubber hardness of the silicone elastomer was 34, as determined with a durometer type A.

Preparation of a Silicone Elastomer Hybrid

The water was removed from the aqueous dispersion 1 by volatilization with a spray dryer Type: B-290, ex Nihon Buchi Co., Ltd., at an inlet temperature of 150 degrees C., an exit temperature of about 80 degrees C. and a feeding rate of the aqueous dispersion of 200 g/hr, to obtain a particulate material, hereinafter referred to as silicone elastomer hybrid 1. The silicone elastomer hybrid 1 thus obtained was spherical under observation with an electron microscope.

Example 2

Preparation of an Aqueous Dispersion of Silicone Elastomer Particles

The process of Example 1 was repeated except that 6 g of polyoxyethylene stearyl ether with 13 moles of EO and an HLB of 13.6, EMULGEN 320P, ex Kao Corporation, was used instead of 3 g of polyoxyethylene stearyl ether, to obtain an aqueous dispersion of silicone elastomer particles, hereinafter referred to as aqueous dispersion 2.

The silicone elastomer particles in the aqueous dispersion 2 thus obtained was spherical under observation with an optical microscope and had a volume-average particle diameter of 6 μm and a 90% volume cumulative diameter (D90) of 8 μm as determined with a particle size distribution measurement instrument using an electric resistance method, Multisizer 3, ex Beckman Coulter, Inc.

Preparation of a Silicone Elastomer Hybrid

The water was removed from the aqueous dispersion 2 by volatilization with a spray dryer, Type: B-290, ex Nihon Buchi Co., Ltd., at an inlet temperature of 150 degrees C., an exit temperature of about 80 degrees C. and a feeding rate of the aqueous dispersion of 200 g/hr, to obtain a particulate material, hereinafter referred to as silicone elastomer hybrid 2. The silicone elastomer hybrid 2 thus obtained was spherical under observation with an electron microscope.

Example 3

Preparation of an Aqueous Dispersion of Silicone Elastomer Particles

The process of Example 1 was repeated except that 3 g of polyoxyethylene stearyl ether with 13 moles of EO and an HLB of 13.6, EMULGEN 320P, ex Kao Corporation, and 2 g of polyoxyethylene stearyl ether with 20 moles of EO and an HLB of 15.3, NIKKOL BS-20, ex Nikko Chemicals Co., Ltd. were used instead of 3 g of polyoxyethylene stearyl ether, to obtain an aqueous dispersion of silicone elastomer particles, hereinafter referred to as aqueous dispersion 3.

The silicone elastomer particles in the aqueous dispersion 3 thus obtained was spherical under observation with an optical microscope and had a volume-average particle diameter of 7 μm and a 90% volume cumulative diameter (D90) of 10 μm as determined with a particle size distribution measurement instrument using an electric resistance method, Multisizer 3, ex Beckman Coulter, Inc.

Preparation of a Silicone Elastomer Hybrid

The water was removed from the aqueous dispersion 3 by volatilization with a spray dryer, Type: B-290, ex Nihon Buchi Co., Ltd., at an inlet temperature of 150 degrees C., an exit temperature of about 80 degrees C. and a feeding rate of the aqueous dispersion of 200 g/hr, to obtain a particulate material, hereinafter referred to as silicone elastomer hybrid 3. The silicone elastomer hybrid 3 thus obtained was spherical under observation with an electron microscope.

Example 4

Preparation of an Aqueous Dispersion of Silicone Elastomer Particles

The process of Example 1 was repeated except that 6 g of polyoxyethylene isostearyl ether with 15 moles of EO and an HLB of 14.3, EMALEX 1815, ex Nihon Emulsion Co., Ltd. was used instead of 3 g of polyoxyethylene stearyl ether, to obtain an aqueous dispersion of silicone elastomer particles, hereinafter referred to as aqueous dispersion 4.

The silicone elastomer particles in the aqueous dispersion 4 thus obtained was spherical under observation with an optical microscope and had a volume-average particle diameter of 5 μm and a 90% volume cumulative diameter (D90) of 6 μm as determined with a particle size distribution measurement instrument using an electric resistance method, Multisizer 3, ex Beckman Coulter, Inc.

Preparation of a Silicone Elastomer Hybrid

The water was removed from the aqueous dispersion 4 by volatilization with a spray dryer, Type: B-290, ex Nihon Buchi Co., Ltd., at an inlet temperature of 150 degrees C., an exit temperature of about 80 degrees C. and a feeding rate of the aqueous dispersion of 200 g/hr, to obtain a particulate material, hereinafter referred to as silicone elastomer hybrid 4. The silicone elastomer hybrid 4 thus obtained was spherical under observation with an electron microscope.

Comparative Example 1

Preparation of an Aqueous Dispersion of Silicone Elastomer Particles

The process of Example 1 was repeated except that 3 g of polyoxyethylene stearyl ether with 20 moles of EO and an HLB of 15.3, NIKKOL BS-20, ex Nikko Chemicals Co., Ltd. was used instead of 3 g of polyoxyethylene stearyl ether, to obtain an aqueous dispersion of silicone elastomer particles, hereinafter referred to as aqueous dispersion 5.

The silicone elastomer particles in the aqueous dispersion 5 thus obtained was spherical under observation with an optical microscope and had a volume-average particle diameter of 10 μm and a 90% volume cumulative diameter (D90) of 21 μm as determined with a particle size distribution measurement instrument using an electric resistance method, Multisizer 3, ex Beckman Coulter, Inc.

Preparation of a Silicone Elastomer Hybrid

The water was removed from the aqueous dispersion 5 by volatilization with a spray dryer, Type: B-290, ex Nihon Buchi Co., Ltd., at an inlet temperature of 150 degrees C., an exit temperature of about 80 degrees C. and a feeding rate of the aqueous dispersion of 200 g/hr, to obtain a particulate material, hereinafter referred to as silicone elastomer hybrid 5. The silicone elastomer hybrid 5 thus obtained was spherical under observation with an electron microscope.

Comparative Example 2

Preparation of an Aqueous Dispersion of Silicone Elastomer Particles

The process of Example 1 was repeated except that 1.2 g of polyoxyethylene stearyl ether with 4 moles of EC and an HLB of 7.9, NIKKOL BS-4, ex Nikko Chemicals Co., Ltd. and 1.8 g of polyoxyethylene stearyl ether with 20 moles of EO and an HLB of 15.3, NIKKOL BS-20, ex Nikko Chemicals Co., Ltd. were used instead of 3 g of polyoxyethylene stearyl ether. In the process of adding the aforesaid two polyoxyethylene stearyl ethers and 50 g water to a solution of methylvinylpolysioxane and methylhydrogenpolysiloxane and, then stirring with a homomixer, an oil-in-water state was not obtained and the reaction product was not emulsified.

Comparative Example 3

Preparation of an Aqueous Dispersion of Silicone Elastomer Particles

The process of Example 1 was repeated except that 1 g of polyoxyethylene behenyl ether with 10 moles of EO and an HLB of 11.5, NIKKOL BB-10, ex Nikko Chemicals Co., Ltd. and 2 g of polyoxyethylene behenyl ether with 20 moles of EO and an HLB of 13.6, NIKKOL BS-20, ex Nikko Chemicals Co., Ltd. were used instead of 3 g of polyoxyethylene stearyl ether to obtain a homogeneous white emulsion.

This emulsion was taken in a one-liter glass flask equipped with a stirrer having anchor type stirring blades, and the temperature thereof was adjusted to 15 to 20 degrees C. Then, added with stirring was a solution consisting of 0.8 g of a solution of a chloroplatinic acid-olefin complex in isododecane, containing 0.5 mass % of platinum, and 1 g of polyoxyethylene sorbitan tristearate, NIKKOL TS-30V, ex Nikko Chemicals Co., Ltd. with 20 moles of EO. The resulting mixture was stirred for 12 hours at the same temperature. Then a lot of agglomerates were formed and an aqueous dispersion of silicone elastomer particles was not obtained.

Regarding aforesaid Examples 1 to 4 and Comparative Examples 1 to 3, the following Table 1 shows the number of the carbon atoms of the alkyl group in the polyoxyethylene alkyl ether, the HLB of the polyoxyethylene alkyl ether, mass % of the polyoxyethylene alkyl ether based on the total mass of the aqueous dispersion obtained, the volume-average particle diameter and the 90% volume cumulative diameter (D90) of the silicone elastomer particle obtained and mass % of the silicone elastomer particles based on the total mass of the aqueous dispersion.

TABLE 1

|  |  | Example 1 | Example 2 | Example 3 | Example 4 | Comparative Example 1 | Comparative Example 2 | Comparative Example 3 |
|---|---|---|---|---|---|---|---|---|
| Polyoxyethylene alkyl ether | Number of the carbon atom of the alkyl group | 18, linear | 18, linear | 18, linear | 18, branched | 18, linear | 18, linear | 22, linear |
|  | HLB | 14.3 | 13.6 | 14.7 | 14.3 | 15.3 | 12.3 | 13.6 |
|  | mass % | 0.3 | 0.6 | 0.5 | 0.6 | 0.3 | 0.3 | 0.3 |
| Silicone elastomer particles | Volume-average particle diameter, μm | 9 | 6 | 7 | 5 | 10 | The reaction product could not be emulsified. | An aqueous dispersion was not obtained. |
|  | 90% volume cumulative diameter (D90), μm | 12 | 8 | 10 | 6 | 21 |  |  |
|  | mass % | 53.3 | 53.0 | 53.1 | 53.0 | 53.3 |  |  |

Example 5 and Comparative Example 4

Evaluations of Feeling in the Use of the Oily Cosmetics

Two oily cosmetics were prepared in the following manner. One comprised the silicone elastomer hybrid prepared in Example 1 and the other comprised the silicone elastomer hybrid prepared in Comparative Example 1. Evenness in spreading and easiness to spread of the cosmetics were evaluated according to the following manners.

[Preparation of Cosmetics]
A: The components (1) to (7) described in the following Table 2 were mixed homogeneously.
B: The mixture obtained in step A above was further mixed with a triple-roll mill to obtain a non-aqueous concealer.

(1) Sensory Evaluation: Evenness in Spreading 1 g of the oily cosmetic was applied on the back of a washed hand of each of ten specialized panelists. The panelists spread the oily cosmetic with their fingers and visually evaluated whether the oily cosmetic was spread evenly. When no unevenness was found, it was given the score of 5. When a little unevenness was found, it was given the score of 3. When remarkable unevenness was found, it was given the score of 1. The scores were summated.

An total score of 40 or larger was evaluated as "A"; 21 to 39, "B"; and 20 or less, "C". The results are as shown in Table 2.

(2) Sensory Evaluation: Easiness to Spread

The oily cosmetic was applied on the faces of the ten specialized panelists. The panelists sensorily evaluated whether the sample was easily spread on their faces. When an oily cosmetic was easy spread, it was given the score of 5. When an oily cosmetic was slightly hard to be spread, it was given the score of 3. When an oily cosmetic was very hard to spread, it was given the score of 1. The scores were summated.

An total score of 40 or larger was evaluated as "A"; 21 to 39, "B"; and 20 or less, "C". The results are as shown in Table 2.

TABLE 2

| Component, mass % | Example 5 | Comparative Example 4 |
|---|---|---|
| 1. Crosslinked polyether-modified silicone [1] | 5 | 5 |
| 2. Crosslinked dimetylpolysiloxane [2] | 55 | 55 |
| 3. Crosslinked dimetylpolysiloxane [3] | 6 | 6 |
| 4. Dimetylpolysiloxane, 6CS [a] | 8 | 8 |
| 5. Solution of Dimetylpolysiloxane and Decamethylcyclopentasiloxane [4] | 5 | 5 |
| 6. Silicone elastomer hybrid prepared in Example 1 | 21 | |
| 7. Silicone elastomer hybrid prepared in Comparative Example 1 | | 21 |
| Total | 100 | 100 |
| Adhesive property | A | C |
| Coating property | A | C |

[1] KSG-210, ex Shin-Etsu Chemical Co., Ltd.
[2] KSG-15, ex Shin-Etsu Chemical Co., Ltd.
[3] KSG-16, ex Shin-Etsu Chemical Co., Ltd.
[4] KF-9028, ex Shin-Etsu Chemical Co., Ltd.
[a] Dimetylpolysiloxane having a dynamic viscosity of 6 mm$^2$/s of at 25 degrees C., ex Shin-Etsu Chemical Co., Ltd.

As shown in Table 2, the cosmetic comprising the present silicone elastomer hybrid had excellent adhesive and coating properties. Further, the effect of concealing pores of skin and wrinkles were good. In contrast, the adhesive and coating properties of the cosmetic comprising the silicone elastomer hybrid prepared in Comparative Example 1 were bad. That is, the cosmetic comprising a silicone elastomer hybrid whose 90% volume cumulative diameter was too large has such problems that the cosmetic formed an uneven coating and had poor spreadability and, therefore, effects as cosmetics were not sufficiently provided.

Cosmetics comprising the present aqueous dispersion or the present silicone elastomer hybrid were prepared and evaluated in the following Examples 6 to 11. Mixing in the following processes was conducted with a disper mixer, T. K. HOMODISPER, ex PRIMIX Corporation, hereinafter referred to as a disper.

Examples 6 and 7

Nonaqueous Concealer

[Preparation of Cosmetics]
A: The components (1) to (7) described in the following Table 3 were mixed homogeneously.
B: The component (8) described in the following Table 3 was added to the mixture obtained in step A and stirred homogeneously to obtain a non aqueous concealer.

TABLE 3

| Component, mass % | Example 6 | Example 7 |
|---|---|---|
| 1. Crosslinked polyether-modified silicone [1] | 5 | 5 |
| 2. Crosslinked dimetylpolysiloxane [2] | 55 | 55 |
| 3. Crosslinked dimetylpolysiloxane [3] | 15 | |
| 4. Dimetylpolysiloxane, 6CS [a] | | 10 |
| 5. Decamethylcyclopentasiloxane | 8 | 8 |
| 6. Solution of Dimetylpolysiloxane and Decamethylcyclopentasiloxane [4] | 5 | 5 |
| 7. Silicone elastomer hybrid-1 | 12 | 5 |
| 8. Hybrid silicone powders [5] | | 12 |
| Total | 100 | 100 |

[1] KSG-210, ex Shin-Etsu Chemical Co., Ltd.
[2] KSG-15, ex Shin-Etsu Chemical Co., Ltd.
[3] KSG-16, ex Shin-Etsu Chemical Co., Ltd.
[4] KF-9028, ex Shin-Etsu Chemical Co., Ltd.
[5] KSP-101, ex Shin-Etsu Chemical Co., Ltd.
[a] Dimetylpolysiloxane having a dynamic viscosity of 6 mm$^2$/s of at 25 degrees C., ex Shin-Etsu Chemical Co., Ltd.

The non aqueous concealers comprising the present silicone elstomer complex had good effect of concealing wrinkles and pores of skin. The cosmetic prepared in Example 6 had a low viscosity and the cosmetic prepared in Example 7 had a high viscosity. Therefore, it is possible to control a viscosity of cosmetics.

Example 8

W/O Type Milky Lotion

[Preparation of a Cosmetic]
A: The components (1) to (7) described in the following Table 4 were mixed with a disper homogeneously.
B: The components (8) to (11) described in the following Table 4 were mixed homogeneously and, then, added to the mixture obtained in step A and emulsified to obtain a W/O type milky lotion.

TABLE 4

| Component, mass % | Example 8 |
|---|---|
| 1. Crosslinked polyether-modified silicone [1] | 3 |
| 2. Crosslinked dimetylpolysiloxane [2] | 9 |
| 3. Crosslinked dimetylpolysiloxane [3] | 20 |

TABLE 4-continued

| Component, mass % | Example 8 |
|---|---|
| 4. Branched polyether-modified silicone [6] | 1 |
| 5. Decamethylcyclopentasiloxane | 25 |
| 6. Mineral oil | 3 |
| 7. Silicone elastomer hybrid-2 | 7 |
| 8. 1,3-Butylene glycol | 3 |
| 9. Sodium citrate | 0.2 |
| 10. Sodium chloride | 0.5 |
| 11. Purified water | 28.3 |
| Total | 100 |

[1] KSG-210, ex Shin-Etsu Chemical Co., Ltd.
[2] KSG-15, ex Shin-Etsu Chemical Co., Ltd.
[3] KSG-16, ex Shin-Etsu Chemical Co., Ltd.
[6] KF-6028P, ex Shin-Etsu Chemical Co., Ltd.

The W/O type milky lotion comprising the present silicone elstomer complex did not show tackiness or oiliness and had good effect of concealing wrinkles and pores of skin.

Example 9

Shake Type Suncut Lotion

[Preparation of a Cosmetic]
A: The components (1) to (8) described in the following Table 5 were mixed with a disper homogeneously.
B: The components (10) to (14) described in the following Table 5 were dissolved each other homogeneously.
C: The solution prepared in step B was added to the mixture prepared in step A, to which the following component (9) was added and, then, stirred homogeneously to obtain a shake type suncut lotion.

TABLE 5

| Component, mass % | Example 9 |
|---|---|
| 1. Crosslinked polyether-modified silicone [1] | 2 |
| 2. Diphenyl siloxy phenyl trimethicone [7] | 5.5 |
| 3. Dimetylpolysiloxane, 6CS [a] | 8 |
| 4. Decamethylcyclopentasiloxane | 14.3 |
| 5. Branched polyether-modified silicone [6] | 2 |
| 6. 2-Ethylhexyl 4-methoxycinnamate | 7.5 |
| 7. Dimethyl distearylammonium hectorite | 0.2 |
| 8. Silicone elastomer hybrid-3 | 1 |
| 9. Zinc oxide dispersion [8] | 30 |
| 10. 1,3-Butylene glycol | 3 |
| 11. Sodium citrate | 0.2 |
| 12. Sodium chloride | 0.5 |
| 13. Ethanol | 5.5 |
| 14. Purified water | 20.3 |
| Total | 100 |

[1] KSG-210, ex Shin-Etsu Chemical Co., Ltd.
[6] KF-6028P, ex Shin-Etsu Chemical Co., Ltd.
[7] KF-56A, ex Shin-Etsu Chemical Co., Ltd.
[8] SPD-Z5, ex Shin-Etsu Chemical Co., Ltd.
[a] Dimetylpolysiloxane having a dynamic viscosity of 6 mm$^2$/s of at 25 degrees C., ex Shin-Etsu Chemical Co., Ltd.

The suncut lotion comprising the present silicone elstomer complex did not show tackiness or oiliness and gave a good feeling in the use.

Examples 10 and 11

Emulsion Type Liquid Foundations

[Preparation of Cosmetics]
A: The components (1) to (10) described in the following Table 6 were mixed with a disper homogeneously.
B: The components (11) to (14) described in the following Table 6 were dissolved each other homogeneously.
C: The solution prepared in step B was added to the mixture prepared in step A, to which another mixture obtained by dispersing the following components (15) to (20) with a three-roller mill was added and mixed homogeneously to obtain an emulsion type liquid foundations.

TABLE 6

| Component, mass % | Example 10 | Example 11 |
|---|---|---|
| 1. Crosslinked polyether-modified silicone [1] | 3.5 | 3.5 |
| 2. Crosslinked dimetylpolysiloxane [2] | 5 | |
| 3. Crosslinked dimetylpolysiloxane [9] | | 5 |
| 4. Branched polyether-modified silicone [6] | 2 | 2 |
| 5. Dimethyl distearylammonium hectorite | 1.2 | 1.2 |
| 6. Triethylhexanoin | 0.25 | 0.25 |
| 7. Dimetylpolysiloxane, 6CS [a] | 6.5 | 12.75 |
| 8. Decamethylcyclopentasiloxane | 22.65 | |
| 9. Dimetylpolysiloxane, 2CS [b] | | 13.6 |
| 10. Silicone elastomer hybrid-2 | 1 | 3 |
| 11. 1,3-Butylene glycol | 5 | 5 |
| 12. Sodium citrate | 0.2 | 0.2 |
| 13. Sodium chloride | 1 | 1 |
| 14. Purified water | 36.7 | 37.5 |
| 15. Triethylhexanoin | 4.75 | 4.75 |
| 16. Silicone modified acrylic polymer [10] | 0.25 | 0.25 |
| 17. Silicone-treated titanium oxide [11] | 8.5 | 8.5 |
| 18. Silicone-treated red iron oxide [11] | 0.41 | 0.41 |
| 19. Silicone-treated yellow iron oxide [11] | 0.97 | 0.97 |
| 20. Silicone-treated black iron oxide [11] | 0.12 | 0.12 |
| Total | 100 | 100 |

[1] KSG-210, ex Shin-Etsu Chemical Co., Ltd.
[2] KSG-15, ex Shin-Etsu Chemical Co., Ltd.
[6] KF-6028P, ex Shin-Etsu Chemical Co., Ltd.
[9] KSG-19, ex Shin-Etsu Chemical Co., Ltd.
[10] KP-578, ex Shin-Etsu Chemical Co., Ltd.
[11] The silicone was KF-9909 ex Shin-Etsu Chemical Co., Ltd.
[a] Dimetylpolysiloxane having a dynamic viscosity of 6 mm$^2$/s of at 25 degrees C., ex Shin-Etsu Chemical Co., Ltd.
[b] Dimetylpolysiloxane having a dynamic viscosity of 2 mm$^2$/s of at 25 degrees C., ex Shin-Etsu Chemical Co., Ltd.

The emulsion type liquid foundation comprising the present silicone elstomer complex did not show tackiness or oiliness and gave a good feeling in the use. The present silicone elastomer complex can be used as a thicker in a low viscous cosmetic, as in the cosmetic prepared in Example 11.

Examples 12 and 13

O/W Type Milky Lotion

[Preparation of Cosmetics]
A: The components (1) to (5) described in the following Table 7 were mixed homogeneously.
B: The components (6) to (9) described in the following Table 7 were mixed homogeneously.
C: The mixture prepared in step B was added to the mixture prepared in step A, and the following component (10) was added thereto to obtain an O/W type milky lotion.

TABLE 7

| Component, mass % | Example 12 | Example 13 |
|---|---|---|
| 1. Ethanol | 17 | 8 |
| 2. 1,3-Butylene glycol | 3 | 3 |
| 3. Polyglycerol-modified silicone [12] | 0.5 | 0.5 |
| 4. Triethylhexanoin | 2 | 2 |
| 5. Hybrid silicone powder [13] | | 5 |

TABLE 7-continued

| Component, mass % | Example 12 | Example 13 |
|---|---|---|
| 6. Ammonium acryloyldimethyltaurate/VP copolymer | 0.4 | 0.4 |
| 7. Xanthane gum | 0.12 | 0.12 |
| 8. Sodium chloride | 0.01 | 0.01 |
| 9. Purified water | 56.97 | 61.97 |
| 10. Aqueous dispersion-1 | 20 | 20 |
| Total | 100 | 100 |

[12] The silicone was KF-6100, ex Shin-Etsu Chemical Co., Ltd.
[13] KSP-100, ex Shin-Etsu Chemical Co., Ltd.

The O/W type milky lotions comprising the present aqueous dispersion did not show tackiness or oiliness and gave a good feeling in the use. The cosmetic prepared in Example 13 comprising the hybrid silicone powder KSP-100 gave refreshed feeling, even though the amount of alcohol was small.

Example 14

Powder Foundation

[Preparation of a Cosmetic]
A: The components (1) and (2) described in the following Table 8 were mixed homogeneously.
B: The components (3) to (10) described in the following Table 8 were mixed homogeneously.
C: The mixture prepared in step A was added to the mixture prepared in step B, and mixed with a Henschel mixer homogeneously. The powder obtained was passed through a mesh and, then, was press-molded with a metal plate to obtain a powder foundation.

TABLE 8

| Component, mass % | Example 14 |
|---|---|
| 1. Squalane | 2 |
| 2. 2-Ethylhexyl 4-methoxycinnamate | 5 |
| 3. Polyethylene | 1.5 |
| 4. Silicone-treated sericite [11] | 38.19 |
| 5. Barium sulfate | 10 |
| 6. Silicone treated titanium dioxide [11] | 9 |
| 7. Silicone elastomer hybrid-4 | 3 |
| 8. Spherical polymethylsilsesquioxane powder [14] | 4.5 |
| 9. Silicone-treated talc [11] | 25 |
| 10. Silicone-treated red iron oxide [11] | 0.46 |
| 11. Silicone-treated yellow iron oxide [11] | 1.07 |
| 12. Silicone-treated black iron oxide [11] | 0.28 |
| Total | 100 |

[11] The silicone was KF-9909, ex Shin-Etsu Chemical Co., Ltd.
[14] KMP-590, ex Shin-Etsu Chemical Co., Ltd.

The powder foundation comprising the present silicone elastomer hybrid had softness and gave a good feeling in the use.

INDUSTRIAL APPLICABILITY

The present aqueous dispersion provides an emulsion having good stability. In the present invention, on account of the use of polyoxyethylene alkyl ether, whose alkyl group has 18 carbon atoms, as a surfactant to the aqueous dispersion, irritation on a skin is decreased, compared to the conventional silicone elastomer particles and aqueous dispersion. A cosmetic comprising the present aqueous dispersion or the silicone elastomer particles gives a good feeling in the use. The present aqueous dispersion and the silicone elastomer particles are usable for various cosmetics.

The invention claimed is:
1. An aqueous dispersion comprising
(A) silicone elastomer particles having a 90% volume cumulative diameter (D90) of 0.3 to 20 μm in an amount of 20 to 80 mass %, based on a total mass of the aqueous dispersion,
(B) at least one polyoxyethylene alkyl ether having an alkyl group having 18 carbon atoms in an amount of 0.01 to 0.6 mass %, based on a total mass of the aqueous dispersion, wherein a hydrophile-lipophile balance (HLB) of the polyoxyethylene alkyl ether is 12.8 to 15.1, and
(C) water in an amount of 19 to 80 mass %, based on a total mass of the aqueous dispersion.
2. The aqueous dispersion according to claim 1, wherein the component (B) is at least one selected from
a compound represented by the following formula (1):

$$C_{18}H_{37}O(CH_2CH_2O)_mH \quad (1)$$

wherein m is an integer of from 2 to 50, and
a compound represented by the following formula (2):

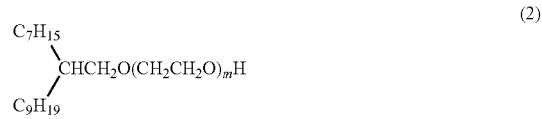

$$\begin{array}{c} C_7H_{15} \\ \phantom{xx}\diagdown \\ \phantom{xxx}CHCH_2O(CH_2CH_2O)_mH \\ \phantom{xx}\diagup \\ C_9H_{19} \end{array} \quad (2)$$

wherein m is an integer of from 2 to 50.
3. The aqueous dispersion according to claim 1 or 2, wherein the alkyl group in the polyoxyethylene alkyl ether (B) is linear.
4. The aqueous dispersion according to claim 1, further comprising (D) at least one selected from polyoxyethylene sorbitan monostearate and polyoxyethylene sorbitan tristearate.
5. The aqueous dispersion according to claim 1, wherein the component (A) is an addition reaction product of an organopolysiloxane having at least two monovalent unsaturated aliphatic groups each bonded to each one silicon atom and an organohydrogenpolysiloxane having at least two hydrogen atoms each bonded to each one silicon atom, provided that at least three monovalent unsaturated aliphatic groups are present in one molecule of said organopolysiloxane and/or at least three hydrogen atoms are present in one molecule of said organohydrogenpolysiloxane.
6. A material comprising
(A) silicone elastomer particles having a 90% volume cumulative diameter (D90) of 0.3 to 20 μm and
(B) at least one polyoxyethylene alkyl ether attaches to a surface of said component (A), wherein the polyoxyethylene alkyl ether has an alkyl group having 18 carbon atoms and a hydrophile-lipophile balance (HLB) of 12.8 to 15.1.
7. The material according to claim 6, wherein the component (B) is at least one selected from
a compound represented by the following formula (1):

$$C_{18}H_{37}O(CH_2CH_2O)_mH \quad (1)$$

wherein m is an integer of from 2 to 50, and a compound represented by the following formula (2):

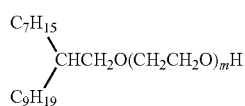

(2)

wherein m is an integer of from 2 to 50.

8. The material according to claim 6 or 7, wherein the alkyl group in the component (B) is linear.

9. The material according to claim 6, further comprising (D) at least one selected from polyoxyethylene sorbitan monostearate and polyoxyethylene sorbitan tristearate.

10. The material according to claim 6, wherein the component (A) is an addition reaction product of an organopolysiloxane having at least two monovalent unsaturated aliphatic groups each bonded to each one silicon atom and an organohydrogenpolysiloxane having at least two hydrogen atoms each bonded to each one silicon atom, provided that at least three monovalent unsaturated aliphatic groups are present in one molecule of said organopolysiloxane and/or at least three hydrogen atoms are present in one molecule of said organohydrogenpolysiloxane.

11. A method for preparing the material according to claim 6, wherein said material is prepared by removing water from an aqueous dispersion comprising
 (A) silicone elastomer particles having a 90% volume cumulative diameter (D90) of 0.3 to 20 μm in an amount of 5 to 80 mass %, based on a total mass of the aqueous dispersion,
 (B) at least one polyoxyethylene alkyl ether having an alkyl group having 18 carbon atoms in an amount of 0.01 to 15 mass %, based on a total mass of the aqueous dispersion, wherein a hydrophile-lipophile balance (HLB) of the polyoxyethylene alkyl ether is 12.8 to 15.1, and
 (C) water in an amount of 19 to 94 mass %, based on a total mass of the aqueous dispersion.

12. The method according to claim 11, wherein the water is removed by spray-drying.

13. A cosmetic comprising the aqueous dispersion according to claim 1.

14. A cosmetic comprising the material according to claim 6.

* * * * *